(12) United States Patent
Ushida

(10) Patent No.: US 11,969,564 B2
(45) Date of Patent: Apr. 30, 2024

(54) GUIDEWIRE

(71) Applicant: ASAHI INTECC CO., LTD., Seto (JP)

(72) Inventor: Keisuke Ushida, Seto (JP)

(73) Assignee: ASAHI INTECC CO., LTD., Seto (JP)

(*) Notice: Subject to any disclaimer, the term of this patent is extended or adjusted under 35 U.S.C. 154(b) by 509 days.

(21) Appl. No.: 16/886,232

(22) Filed: May 28, 2020

(65) Prior Publication Data

US 2020/0289795 A1 Sep. 17, 2020

Related U.S. Application Data

(63) Continuation of application No. PCT/JP2018/004193, filed on Feb. 7, 2018.

(51) Int. Cl.
*A61M 25/09* (2006.01)
*A61M 25/00* (2006.01)

(52) U.S. Cl.
CPC ..... *A61M 25/09* (2013.01); *A61M 2025/0046* (2013.01); *A61M 2025/09091* (2013.01); *A61M 2025/09133* (2013.01)

(58) Field of Classification Search
CPC ................ A61M 25/008; A61M 25/09; A61M 2025/0046; A61M 2025/09083; A61M 2025/09175; A61M 2025/09058–09091; A61M 2025/09108; A61M 2025/09133–09191
See application file for complete search history.

(56) References Cited

U.S. PATENT DOCUMENTS

| | | | | |
|---|---|---|---|---|
| 5,171,383 A * | 12/1992 | Sagae | ................... | A61M 25/09 148/563 |
| 5,287,858 A * | 2/1994 | Hammerslag | ......... | A61M 25/09 600/585 |
| 6,019,736 A * | 2/2000 | Avellanet | .............. | A61M 25/09 604/103.1 |
| 6,387,060 B1 * | 5/2002 | Jalisi | ..................... | A61M 25/09 600/585 |
| 2006/0047224 A1 | 3/2006 | Grandfield | | |
| 2008/0183182 A1 | 7/2008 | Satou et al. | | |
| 2009/0005706 A1 * | 1/2009 | Miyata | .................. | A61M 25/09 600/585 |

(Continued)

FOREIGN PATENT DOCUMENTS

| | | |
|---|---|---|
| JP | 2007-135645 A | 6/2007 |
| JP | 2008-161589 A | 7/2008 |

(Continued)

OTHER PUBLICATIONS

Wong, Garrett L. "Second Generation Design of an Operator Independent Teflon Coating Adhesion Tester for Coronary Guidewires." (2014). (Year: 2014).*

Primary Examiner — Alex M Valvis
Assistant Examiner — Nidhi N Patel
(74) Attorney, Agent, or Firm — Oliff PLC

(57) ABSTRACT

A guidewire comprises a core shaft, a coil body covering a distal end portion of the core shaft, and a coating agent covering an outer periphery of the coil body, wherein the coil body includes a distal coil body disposed on a distal side of the coil body, and a proximal coil body disposed on a proximal side of the distal coil body, a surface roughness of the proximal coil body is higher than a surface roughness of the distal coil body.

9 Claims, 8 Drawing Sheets

(56) References Cited

U.S. PATENT DOCUMENTS

| | | | |
|---|---|---|---|
| 2009/0163833 A1* | 6/2009 | Kinoshita | A61M 25/09 |
| | | | 600/585 |
| 2012/0253319 A1 | 10/2012 | Matsuo | |
| 2013/0006221 A1 | 1/2013 | Koike | |
| 2016/0074631 A1 | 3/2016 | Otani | |
| 2018/0064913 A1* | 3/2018 | Ushida | A61M 25/09 |

FOREIGN PATENT DOCUMENTS

| | | |
|---|---|---|
| JP | 4980605 B2 | 7/2012 |
| JP | 2013-013449 A | 1/2013 |
| JP | 5360840 B2 | 12/2013 |
| JP | 2015-13005 A | 1/2015 |
| JP | 6046804 B2 | 12/2016 |

* cited by examiner

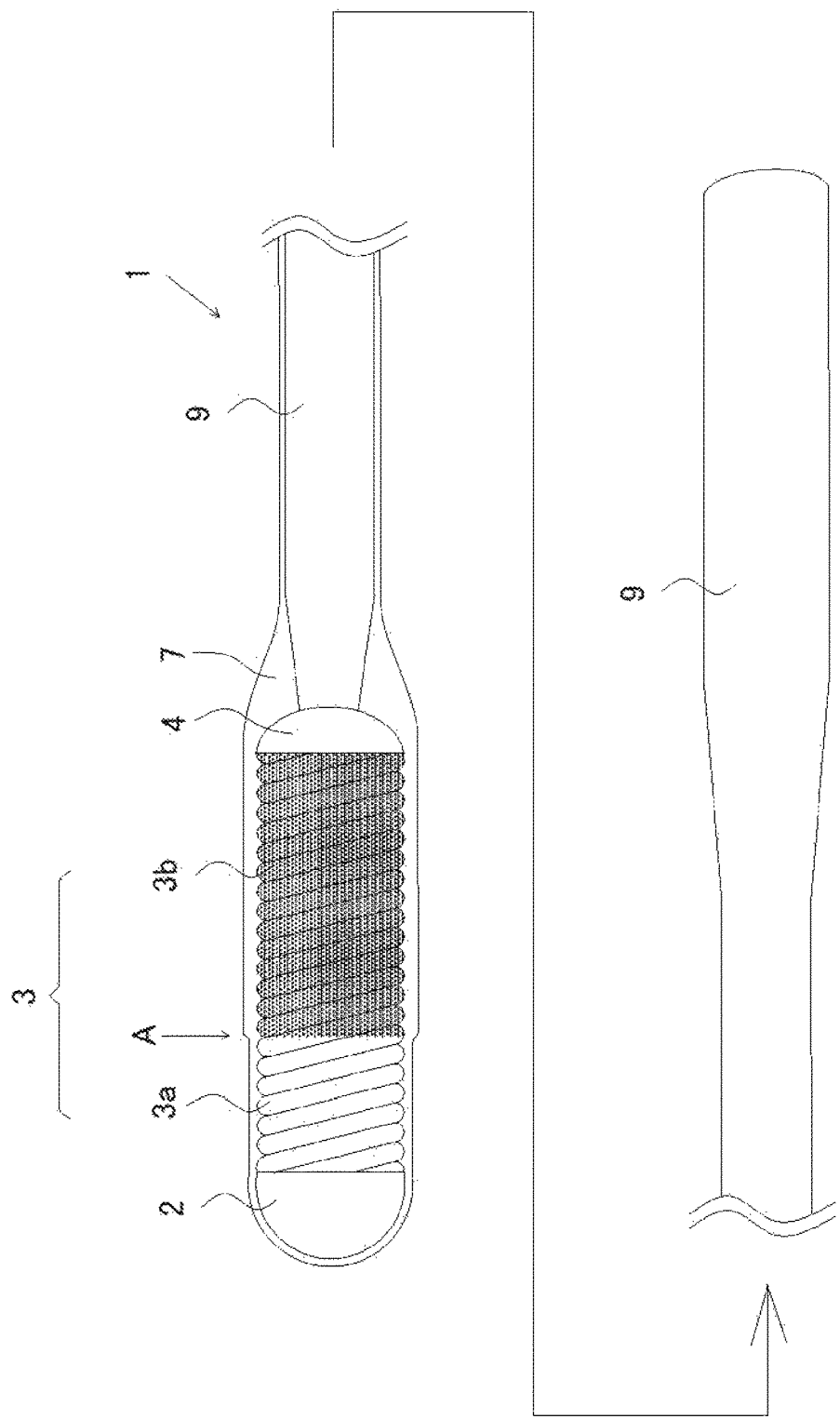

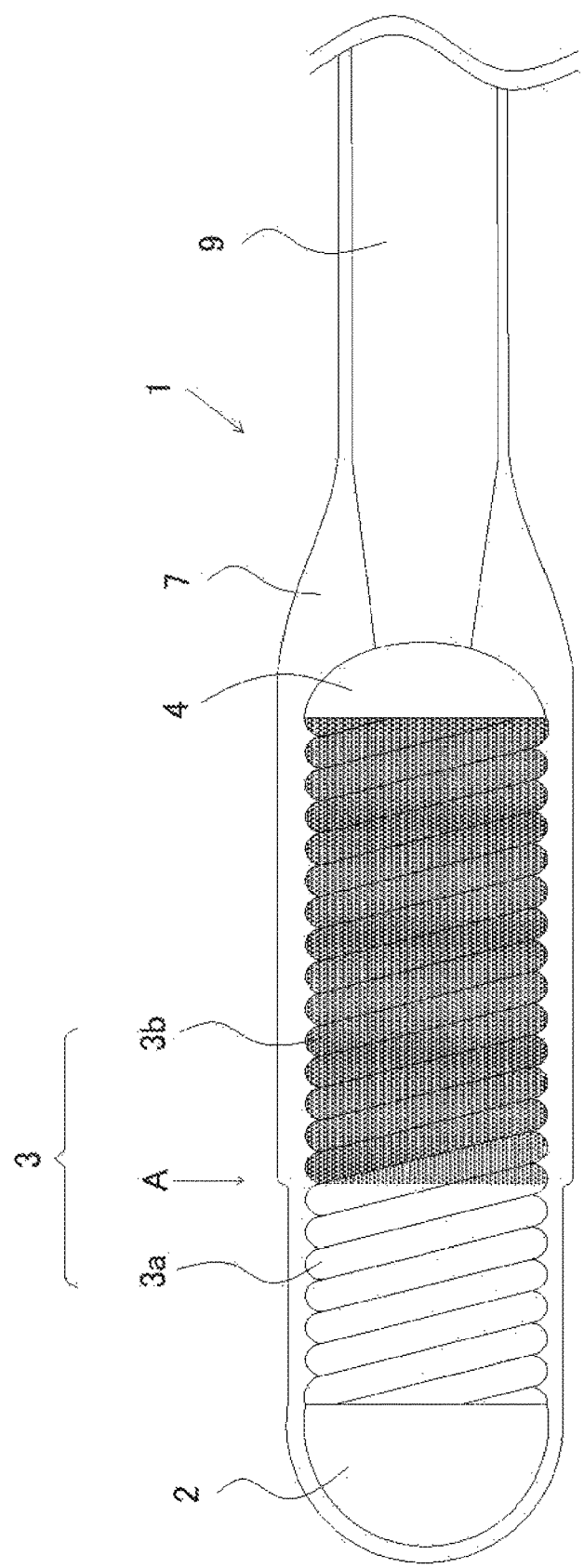

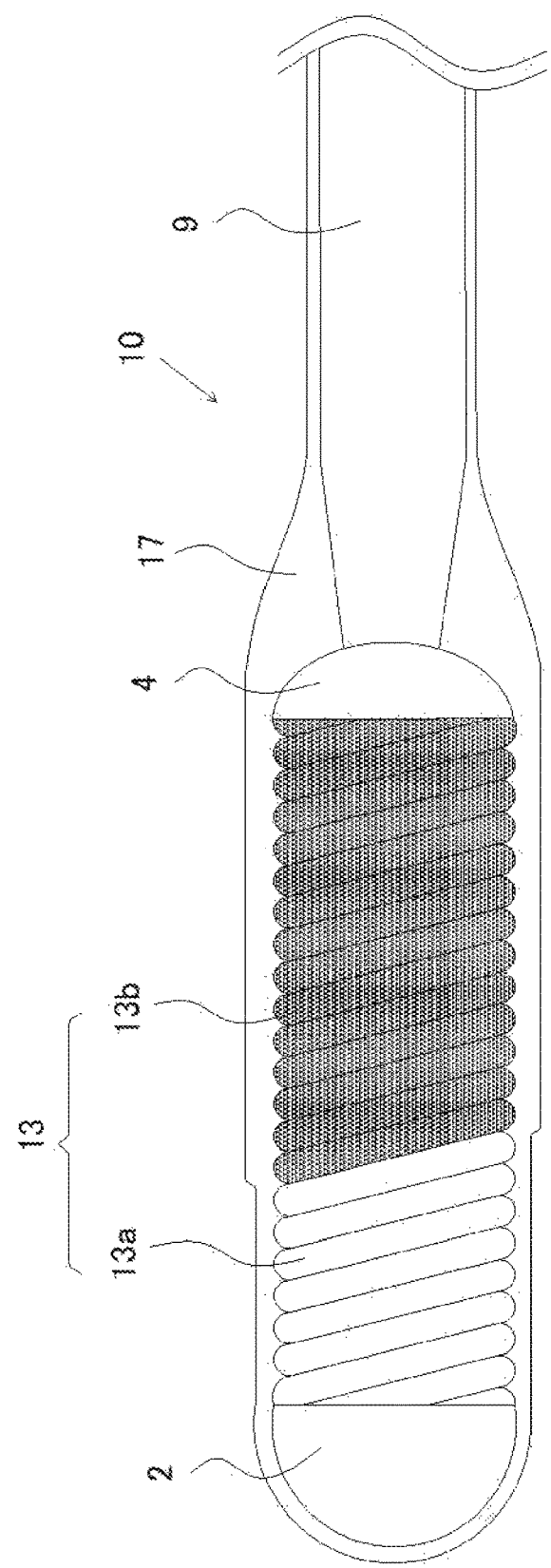
[FIG.03]

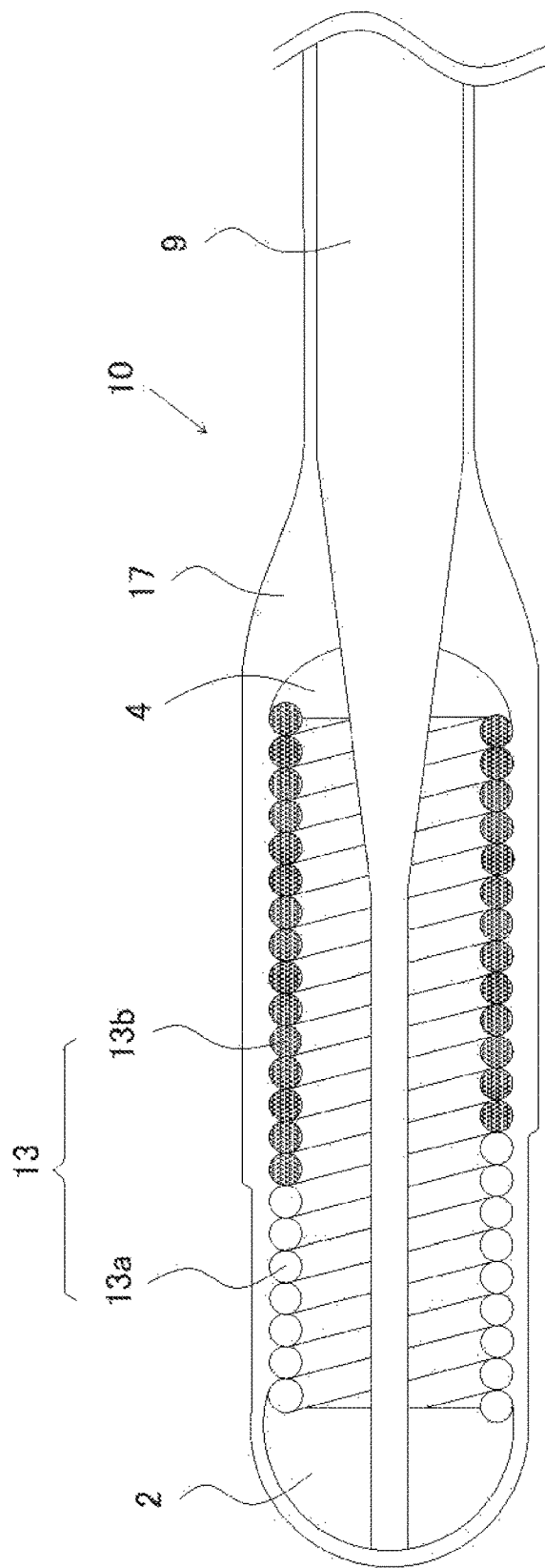
[FIG.04]

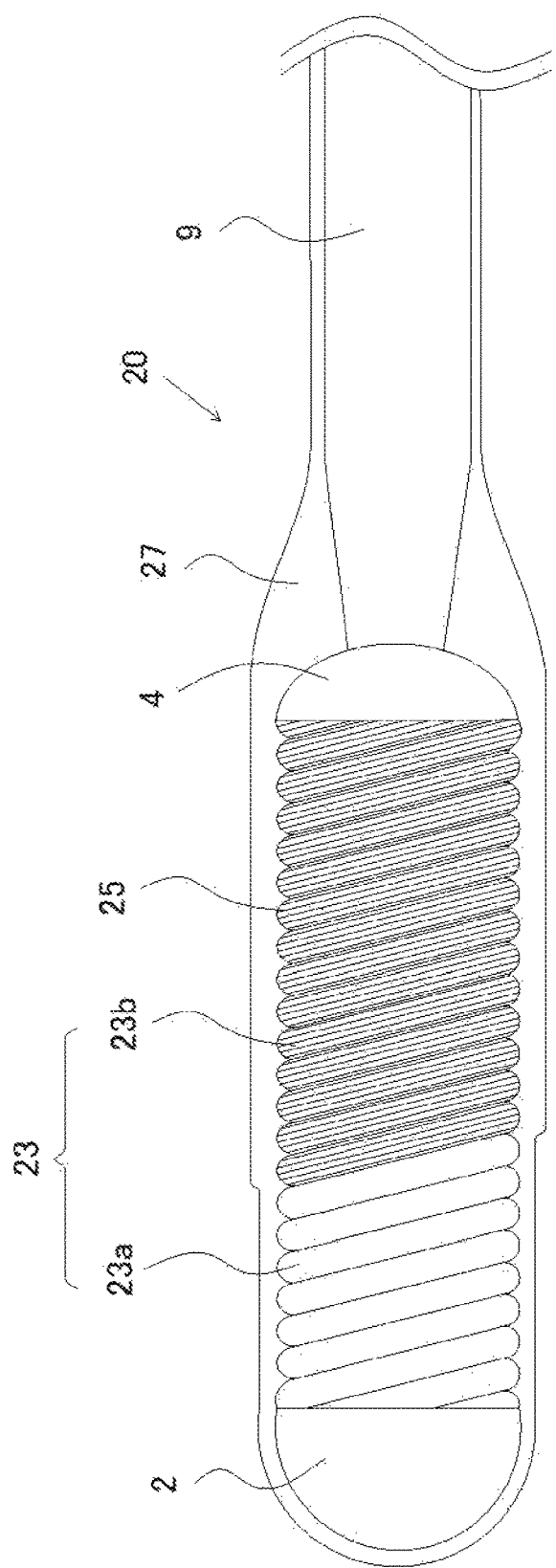
[FIG.05]

[FIG.06]
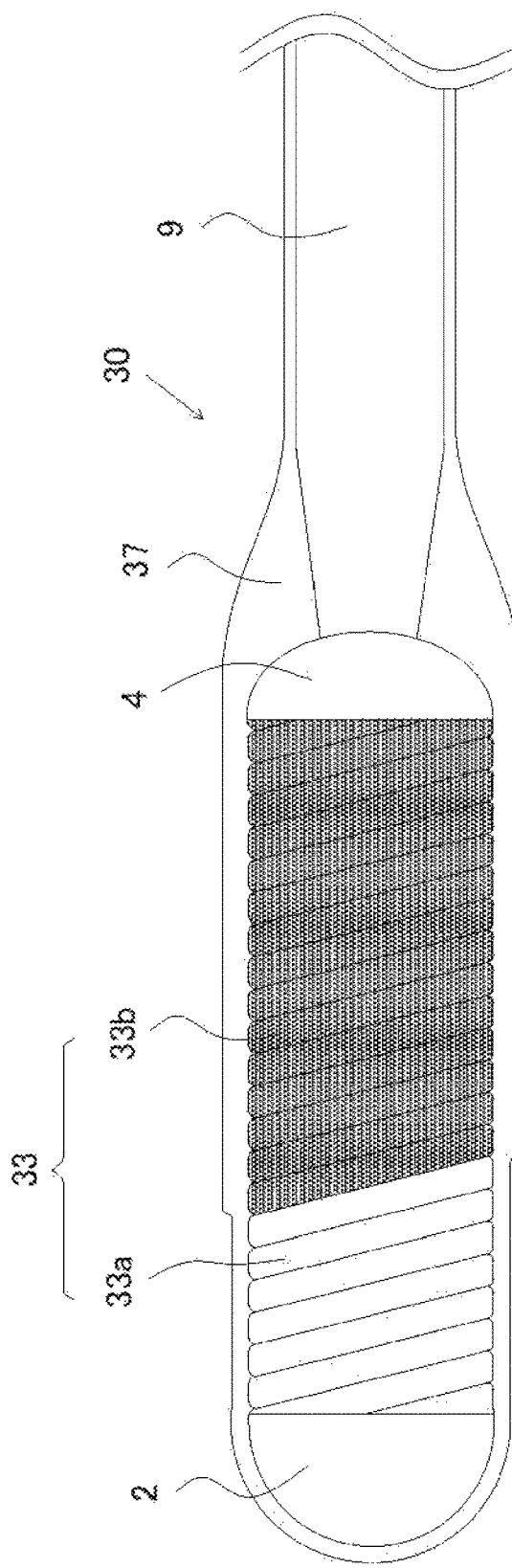

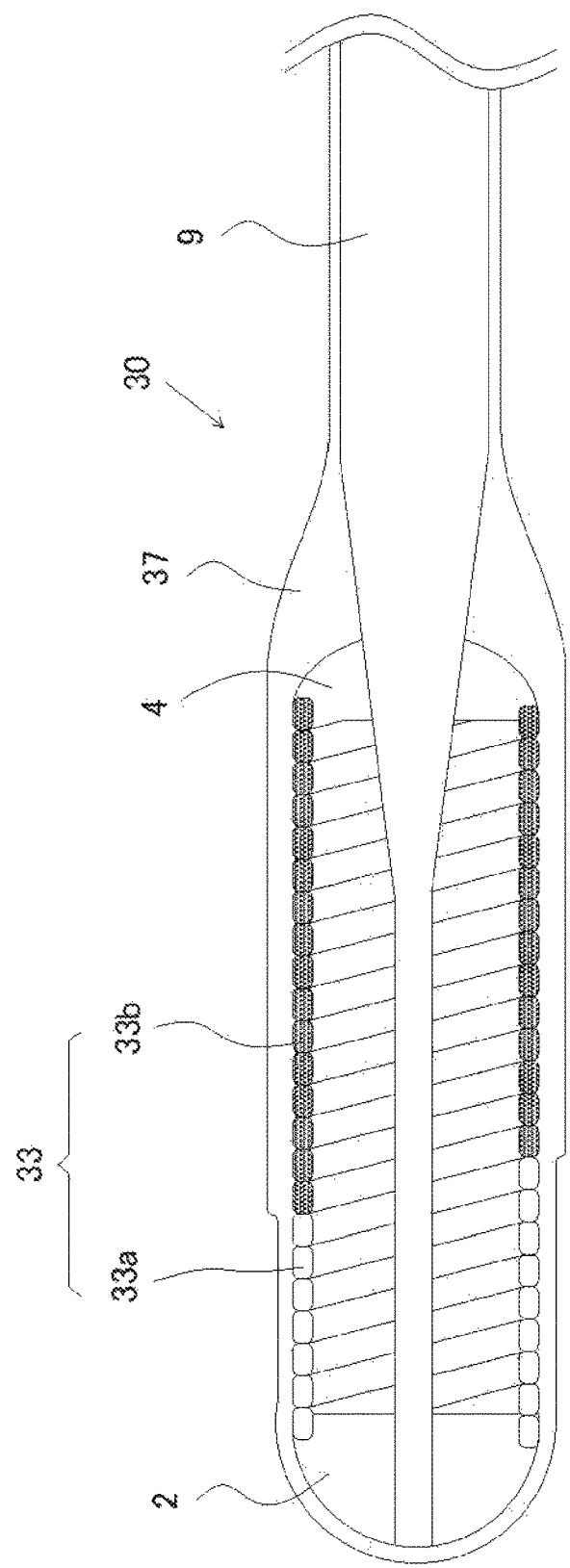
[FIG.07]

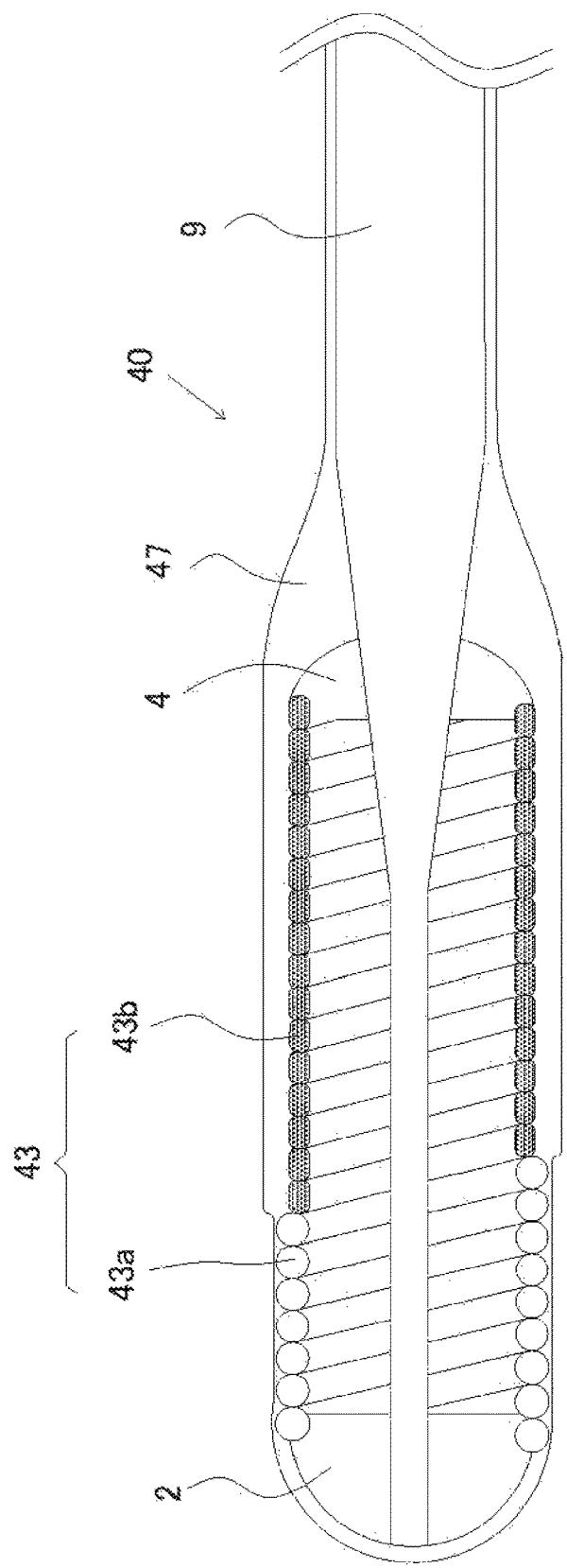

GUIDEWIRE

CROSS REFERENCE TO RELATED APPLICATION

This application is a continuation of International Application No. PCT/JP2018/004193 filed Feb. 7, 2018. The entire content of the priority application is incorporated herein by reference.

TECHNICAL FIELD

The present invention relates to a medical device, and specifically to a medical guidewire.

BACKGROUND ART

In related art, a variety of guidewires guiding a catheter or the like that is used by being inserted into tubular organs such as a blood vessel, a gastrointestinal tract and a ureter or body tissues for treatment or examination has been developed. For example, Patent Document 1 discloses a guidewire comprising a wire body, a coil body including a distal coil body and a proximal coil body covering a distal end portion of the wire body, and a resin coating layer provided on an outer periphery of the coil body consisting of the distal coil body and the proximal coil body (see FIG. 1 etc.).

Patent Document 1: Japanese Patent Application Publication No. 2007-135645 A

SUMMARY

Technical Problems

A resin coating layer covering an outer periphery of a guidewire generally reduces friction of the guidewire and improves operability of the guidewire by improving slidability of the guidewire. That is also described in Patent Document 1 regarding a resin coating layer described therein (see paragraph [0116]).

However, an entire coil body has same slidability and flexibility, since the resin coating layer described in Patent Document 1 is formed with a substantially uniform thickness throughout the coil body. In the case of forming the entire coil body with a thick film thickness, there is a problem that flexibility of a distal end of the coil body may be impaired, in the case of forming the entire coil body with a thin film thickness, there is a problem that slidability in a proximal side of the coil body may be impaired.

Moreover, it is conceivable to set a good film thickness throughout the coil body, but tolerable range of the good film thickness is very narrow, there is a problem that manufacturing yield of the guidewire is poor.

The present disclosure has been made in response to forgoing problems of the related technique and is intended to provide a guidewire capable of being easily manufactured and providing good slidability of the guidewire and good flexibility of a distal end of the guidewire.

Solution for Problems

It is characterized in that, to solve the foregoing problems, a guidewire according to a first aspect of the present disclosure comprises a core shaft, a coil body covering a distal end portion of the core shaft, and a coating agent covering an outer periphery of the coil body, wherein the coil body includes a distal coil body disposed on a distal side of the coil body, and a proximal coil body disposed on a proximal side of the distal coil body, a surface roughness of the proximal coil body is higher than a surface roughness of the distal coil body.

A second aspect of the present disclosure is characterized in that, in the guidewire according to the first aspect, a groove is formed along a longitudinal direction of a wire included in the proximal coil body on a surface of the proximal coil body.

A third aspect of the present disclosure is characterized in that, in the guidewire according to the first aspect or the second aspect, the wire included in the proximal coil body is rectangular shape in cross section.

Furthermore, a fourth aspect of the present disclosure is characterized in that, in the guidewire according to the third aspect, a wire included in the distal coil body is circular shape in cross section.

Advantageous Effects

According to the guidewire of the first aspect of the present disclosure, as a guidewire comprises a core shaft, a coil body covering a distal end portion of the core shaft, and a coating agent covering an outer periphery of the coil body, wherein the coil body includes a distal coil body disposed on a distal side of the coil body, and a proximal coil body disposed on a proximal side of the distal coil body, a surface roughness of the proximal coil body is higher than a surface roughness of the distal coil body, when the coating agent is applied to a surface of the coil body, it is capable of improving slidability of the guidewire by forming a thick coating film with high adhesion to the proximal coil body at a proximal side of the coil body, and improving flexibility of a distal end of the guidewire wire by forming a thin coating film to the distal coil body at a distal side of the coil body.

According to the second aspect of the present disclosure, in the guidewire according to the first aspect, as a guidewire further comprises a groove formed along a longitudinal direction of a wire included in the proximal coil body on a surface of the proximal coil body, in addition to the effects of the guidewire of the first aspect of the present disclosure, it is capable of easily forming the proximal coil body with high surface roughness only by passing a wire included in the proximal coil body through a die with an uneven inner circumference. And it is capable of easily improving slidability of the guidewire by forming a thick coating film with high adhesion to the proximal coil body at a proximal side of the coil body, and easily improving flexibility of a distal end of the guidewire wire by forming a thin coating film to the distal coil body at a distal side of the coil body.

According to the third aspect of the present disclosure, in the guidewire according to the first aspect or the second aspect, as a wire included in the proximal coil body has a rectangular shape in cross section, in addition to the effects of the guidewire of the first aspect or the second aspect of the present disclosure, when an inner surface of the distal coil body is aligned with an inner surface of the proximal coil body, it is capable of increasing a thickness of the coating film of the proximal coil body.

According to the fourth aspect of the present disclosure, in the guidewire according to the third aspect, as a wire included in the distal coil body has a circular shape in cross section, in addition to the effects of the guidewire of the third aspect of the present disclosure, wires included in the distal coil body are point contact with each other, it is capable of further improving flexibility of a distal end of the guidewire.

BRIEF DESCRIPTION OF THE DRAWINGS

FIG. 1 is a schematic view of a guidewire according to a first embodiment of the present disclosure.

FIG. 2 is a distal end enlarged view of the guidewire of the first embodiment.

FIG. 3 is a distal end enlarged view of a guidewire of a second embodiment.

FIG. 4 is a distal end vertical sectional view of the guidewire of the second embodiment.

FIG. 5 is a distal end enlarged view of a guidewire of a third embodiment.

FIG. 6 is a distal end enlarged view of a guidewire of a fourth embodiment.

FIG. 7 is a distal end vertical sectional view of the guidewire of the fourth embodiment.

FIG. 8 is a distal end vertical sectional view of a guidewire of a fifth embodiment.

DETAILED DESCRIPTION

Hereinafter, embodiments of the present disclosure will be described with reference to the drawings.

First Embodiment

First of all, a first embodiment of the present disclosure will be described. FIG. 1 is a schematic view of a guidewire according to a first embodiment of the present disclosure, and FIG. 2 is a distal end enlarged view of the guidewire of the first embodiment.

As shown in FIG. 1, a guidewire 1 of the present embodiment includes a core shaft 9, a coil body 3 covering a distal portion of the core shaft 9, and a coating agent 7 covering an outer periphery of the coil body 3.

The core shaft 9 is a rod-like member of circular cross-section which is reduced in diameter toward a distal end from a proximal end of the core shaft 9, is an elongate flexible member. Material of the core shaft 9 is not particularly limited as long as it is biocompatible material such as stainless steel, Ni—Ti-based alloys, cobalt based alloys or the like. Stainless steel may be used in the present embodiment.

The coil body 3 is a cylindrical hollow coil body formed by winding one or more metal wires, a distal end of the coil body 3 is joined to the core shaft 9 by brazing material 2, and a proximal end of the coil body 3 is joined to the core shaft 9 by brazing material 4.

The coil body 3 of the present embodiment is formed from two coil bodies consisting of a distal coil body 3a disposed on a distal side in the coil body 3 and a proximal coil body 3b disposed on a proximal side of the distal coil body 3a. Incidentally, the distal coil body 3a of the present embodiment means a coil body located on a distal side from an intermediate position A of the coil body 3 in the coil body 3, and the proximal coil body 3b of the present embodiment means a coil body located on a proximal side from the intermediate position A of the coil body 3 in the coil body 3.

Further, a surface roughness of the proximal coil body 3b is higher than a surface roughness of the distal coil body 3a in the present embodiment. Incidentally, an area of the proximal coil body 3b is illustrated by hatching in FIGS. 1 and 2 in order to show that the surface roughness of the proximal coil body 3b is higher than the surface roughness of the distal coil body 3a.

Concerning adjustment of the surface roughness, for example, the surface roughness of the proximal coil body 3b can be made higher than the surface roughness of the distal coil body 3a by performing a known surface treatment such as a blasting throughout the coil body 3 after masking a portion of the distal coil body 3a in the coil body 3.

The material of a wire included in the coil body 3 is not particularly limited as long as it is biocompatible material such as tungsten, Ni—Ti-based alloy or the like, and stainless steel may be used in the present embodiment. The material of wires included in the distal coil body 3 and the proximal coil body 3b may also be of the same stainless steel.

Further, the material of the brazing material 2 and the brazing material 4 is not particularly limited as long as it is biocompatible material such as gold-tin brazing metal, silver-tin brazing material or the like, and silver-tin brazing material may be used in the present embodiment.

The coating agent 7 covers the outer periphery of the coil body 3 and the core shaft 9 as described above, and the coating agent 7 of the present embodiment has a feature that the coating thickness of the proximal coil body 3b located on a proximal side from an intermediate position A of the coil body 3 is larger than the coating thickness of the distal coil body 3a located on a distal side from the intermediate position A of the coil body 3 as shown in FIGS. 1 and 2.

Incidentally, the difference between the coating thickness of the proximal coil body 3b and the coating thickness of the distal coil body 3a in the present embodiment may be, for example, about several μm-10 μm, and it is illustrated exaggeratedly to facilitate understanding of the difference in FIGS. 1 and 2.

Since the surface roughness of the proximal coil body 3b is higher than the surface roughness of the distal coil body 3a, when the coating agent 7 is applied on the surface of the coil body 3, the coating thickness of the proximal coil body 3b automatically becomes larger than the coating thickness of the distal coil body 3a. That is a reason why the coating thickness of the proximal coil body 3b is larger than the coating thickness of the distal coil body 3a in the present embodiment.

In this case, since the surface roughness of the proximal coil body 3b is high, it is capable of improving the adhesion between the proximal coil body 3b and the coating agent 7, and improving slidability of the guidewire 1.

On the other hand, it is capable of securing a good flexibility of the distal end of the guidewire 1 by applying the coating agent 7 in a thin layer on the distal coil body 3a at the distal side of the coil body 3.

Incidentally, the coating agent 7 is preferably formed by material such as polyvinyl alcohol, polyvinyl pyrrolidone, polyethylene glycol, polyacrylamide, polyacrylic acid, sodium polyacrylate, poly (2-hydroxyethyl methacrylate), maleic anhydride copolymer, ethylene-vinyl alcohol copolymer, 2-methacryloyloxyethyl phosphorylcholine or a copolymer thereof, (2-hydroxyethyl methacrylate)—styrene block copolymer, various synthetic polypeptides, collagen, hyaluronic acid, cellulose-based polymer, and mixtures thereof.

According to the guidewire 1 of the present embodiment, as a guidewire 1 comprises a core shaft 9, a coil body 3 covering a distal end portion of the core shaft 9, and a coating agent 7 covering an outer periphery of the coil body 3, wherein the coil body 3 includes a distal coil body 3a disposed on a distal side of the coil body 3, and a proximal coil body 3b disposed on a proximal side of the distal coil body 3a, a surface roughness of the proximal coil body 3b is higher than a surface roughness of the distal coil body 3a, when the coating agent 7 is applied to a surface of the coil body 3, it is capable of improving slidability of the guidewire 1 by forming a thick coating film with high adhesion to the proximal coil body 3b at a proximal side of the coil body 3, and improving flexibility of a distal end of the guidewire wire 1 by forming a thin coating film to the distal coil body 3a at a distal side of the coil body 3.

Second Embodiment

Next, a second embodiment of the present disclosure will be described. FIG. 3 is a distal end enlarged view of a guidewire of a second embodiment, and FIG. 4 is a distal end vertical sectional view of the guidewire of the second embodiment.

In the present embodiment, portions common to the first embodiment will be denoted by the same reference numerals, and descriptions of the portions will be omitted.

As shown in FIG. 3, a guidewire 10 of the present embodiment includes a core shaft 9, a coil body 13 covering a distal portion of the core shaft 9, and a coating agent 17 covering an outer periphery of the coil body 13.

The coil body 13 is a cylindrical hollow coil body formed by winding one or more metal wires, a distal end of the coil body 13 is joined to the core shaft 9 by brazing material 2, and a proximal end of the coil body 13 is joined to the core shaft 9 by brazing material 4.

The coil body 13 of the present embodiment is formed from two coil bodies consisting of a distal coil body 13a disposed on a distal side in the coil body 13 and a proximal coil body 13b disposed on a proximal side of the distal coil body 13a. Incidentally, a distal end of a wire included in the proximal coil body 13b of the present embodiment is joined to a proximal end of a wire included in the distal coil body 13a. Accordingly, a boundary between the distal coil body 13a and the proximal coil body 13b inclines obliquely along a twist angle of the coil body 13 as shown in FIGS. 3 and 4.

Further, a hardness of the distal coil body 13a is lower than a hardness of the proximal coil body 13b in the present embodiment. Incidentally, an area of the proximal coil body 13b is illustrated by hatching in FIGS. 3 and 4 in order to show that the surface roughness of the proximal coil body 13b is higher than the surface roughness of the distal coil body 13a as described below.

A material similar to that of the coil body 3 of the first embodiment may be used for the material of a wire included in the coil body 13. Platinum may be used in the distal coil body 13a and stainless steel may be used in the proximal coil body 13b in the present embodiment.

Incidentally, the distal coil body 13a is not limited as long as it has a hardness less than a hardness of the proximal coil body 13b. For example, as described above, they may be of different kinds of metals, such as platinum and stainless steel, or they may be of metals of different hardnesses by wire drawing or heat treatment in the same kind of metals.

The coating agent 17 covers the outer periphery of the coil body 13 and the core shaft 9 as described above, and the coating agent 17 of the present embodiment has a feature that the coating thickness of a range of the proximal coil body 13b is larger than the coating thickness of a range of the distal coil body 13a as shown in FIGS. 3 and 4.

Incidentally, the difference between the coating thickness of the range of the proximal coil body 13b and the coating thickness of the range of the distal coil body 13a in the present embodiment may be, for example, about several µm-10 µm, and it is illustrated exaggeratedly to facilitate understanding of the difference in FIGS. 3 and 4.

Since the surface roughness of the proximal coil body 13b is higher than the surface roughness of the distal coil body 13a, the coating thickness of the proximal coil body 13b becomes larger than the coating thickness of the distal coil body 13a.

Also, the following process is performed to the coil body 13 in order to increase the surface roughness of the proximal coil body 13b than the surface roughness of the distal coil body 13a in the present embodiment.

That is, first of all, scratches (unevennesses) are formed on a surface of a wire included in the proximal coil body 13b and the distal coil body 13a in a process of wire drawing using a die. Then a surface of the distal coil body 13a is smoothed by swaging the distal coil body 13a having lower hardness than the proximal coil body 13b. Accordingly, the surface roughness of the proximal coil body 13b becomes higher than the surface roughness of the distal coil body 13a.

Accordingly, the proximal coil body 13b is illustrated by hatching, but the distal coil body 13a is not illustrated by hatching in FIGS. 3 and 4. That does not mean that the surface of the distal coil body 13a is flat, but means merely that the surface roughness of the distal coil body 13a is smaller than the surface roughness of the proximal coil body 13b.

Thereafter when the coating agent 17 is applied on the surface of the coil body 13, the coating thickness of a range of the proximal coil body 13b automatically becomes larger than the coating thickness of a range of the distal coil body 13a.

In this case, since the surface roughness of the proximal coil body 13b is high, it is capable of improving the adhesion between the proximal coil body 13b and the coating agent 17, and improving slidability of the guidewire 10.

On the other hand, it is capable of securing a good flexibility of the distal end of the guidewire 10 by applying the coating agent 17 in a thin layer on the distal coil body 13a at the distal side of the coil body 13.

Incidentally, the coating agent 17 may use the same material as the coating agent 7 of the first embodiment.

According to the guidewire 10 of the present embodiment, as a guidewire 10 comprises a core shaft 9, a coil body 13 covering a distal end portion of the core shaft 9, and a coating agent 17 covering an outer periphery of the coil body 13, wherein the coil body 13 includes a distal coil body 13a disposed on a distal side of the coil body 13, and a proximal coil body 13b disposed on a proximal side of the distal coil body 13a, and a hardness of the distal coil body 13a is lower than a hardness of the proximal coil body 13b, the surface roughness of the proximal coil body 13b may be easily higher than the surface roughness of the distal coil body 13a. Accordingly it is capable of improving slidability of the guidewire 10 by forming easily a thick coating film with high adhesion to the proximal coil body 13b at a proximal side of the coil body 13, and improving flexibility of a distal end of the guidewire wire 10 by forming a thin coating film to the distal coil body 13a at a distal side of the coil body 13.

Third Embodiment

Next, a third embodiment of the present disclosure will be described. FIG. 5 is a distal end enlarged view of a guidewire of a third embodiment.

In the present embodiment, portions common to the first embodiment will be denoted by the same reference numerals, and descriptions of the portions will be omitted.

As shown in FIG. 5, a guidewire 20 of the present embodiment includes a core shaft 9, a coil body 23 covering a distal portion of the core shaft 9, and a coating agent 27 covering an outer periphery of the coil body 23.

The coil body 23 is a cylindrical hollow coil body formed by winding one or more metal wires, a distal end of the coil body 23 is joined to the core shaft 9 by brazing material 2, and a proximal end of the coil body 23 is joined to the core shaft 9 by brazing material 4.

The coil body 23 of the present embodiment is formed from two coil bodies consisting of a distal coil body 23a disposed on a distal side in the coil body 23 and a proximal coil body 23b disposed on a proximal side of the distal coil body 23a. Incidentally, a distal end of a wire included in the proximal coil body 23b of the present embodiment is joined to a proximal end of a wire included in the distal coil body 23a. Accordingly, a boundary between the distal coil body 23a and the proximal coil body 23b inclines obliquely along a twist angle of the coil body 23 as shown in FIG. 5.

Further, a plurality of grooves 25 are formed on the surface of wires included in the proximal coil body 23b along the longitudinal direction of the wires as shown in FIG. 5 in the present embodiment.

Incidentally, the grooves 25 are formed on an entire surface of a wire included in the proximal coil body 23b. The grooves 25 may also be formed on a part of the surface of the wire included in the proximal coil body 23b. However, if the grooves 25 are formed on the entire surface of the wire included in the proximal coil body 23b, it may further increase the thickness of a coating agent described later.

A material similar to that of the coil body 3 of the first embodiment may be used for the material of a wire included in the coil body 23. Stainless steel may be used in the distal coil body 23a and the proximal coil body 23b in the present embodiment.

The coating agent 27 covers the outer periphery of the coil body 23 and the core shaft 9 as described above, and the coating agent 27 of the present embodiment has a feature that the coating thickness of a range of the proximal coil body 23b is larger than the coating thickness of a range of the distal coil body 23a as shown in FIG. 5.

Incidentally, the difference between the coating thickness of the range of the proximal coil body 23b and the coating thickness of the range of the distal coil body 23a in the present embodiment may be, for example, about several μm-10 μm, and it is illustrated exaggeratedly to facilitate understanding of the difference in FIG. 5.

Since a plurality of grooves 25 are formed on the surface of wires included in the proximal coil body 23b along the longitudinal direction of the wires in the present embodiment, the surface roughness of the proximal coil body 23b is higher than the surface roughness of the distal coil body 23a, and the coating thickness of the range of the proximal coil body 23b becomes larger than the coating thickness of the range of the distal coil body 23a.

Thereafter when the coating agent 27 is applied on the surface of the coil body 23, the coating thickness of the proximal coil body 23b automatically becomes larger than the coating thickness of the distal coil body 23a.

Since a plurality of grooves 25 are formed on the surface of wires included in the proximal coil body 23b along the longitudinal direction of the wires, it is capable of improving the adhesion between the proximal coil body 23b and the coating agent 27, and improving slidability of the guidewire 20.

On the other hand, it is capable of securing a good flexibility of the distal end of the guidewire 20 by applying the coating agent 27 in a thin layer on the distal coil body 23a at the distal side of the coil body 23.

Incidentally, the coating agent 27 may use the same material as the coating agent 7 of the first embodiment.

According to the guidewire 20 of the present embodiment, as a guidewire 20 comprises a core shaft 9, a coil body 23 covering a distal end portion of the core shaft 9, and a coating agent 27 covering an outer periphery of the coil body 23, wherein the coil body 23 includes a distal coil body 23a disposed on a distal side of the coil body 23, and a proximal coil body 23b disposed on a proximal side of the distal coil body 23a, and a plurality of grooves 25 are formed on the surface of wires included in the proximal coil body 23b along the longitudinal direction of the wires, it is capable of forming the proximal coil body 23b having high surface roughness only by passing a wire included in the proximal coil body 23b through a die with an uneven inner circumference. Accordingly it is capable of improving slidability of the guidewire 20 by forming easily a thick coating film with high adhesion to the proximal coil body 23b at a proximal side of the coil body 23, and improving flexibility of a distal end of the guidewire 20 by forming a thin coating film to the distal coil body 23a at a distal side of the coil body 23.

The distal coil body 23a and the proximal coil body 23b in the present embodiments have been described as consisting of the same stainless steel. However, they may be set such that the hardness of the distal coil body 23a is lower than the hardness of the proximal coil body 23b and grooves 25 may be formed on the surface of wires included in the proximal coil body 23b along the longitudinal direction of the wires as described in the second embodiment. Further, they may be made by well-known surface treatment methods such as blasting processing being applied to the entire coil body 23 after masking a portion of the distal coil body 23a in the coil body 23 as described in the first embodiment.

In that case, in addition to the effect of the guidewire 20 of the present embodiment, the guidewire 20 may achieve effects of the guidewire of the first embodiment and the guidewire of the second embodiment. For example, it is capable of forming easily the proximal coil body 23b having high surface roughness only by passing a wire included in the proximal coil body 23b through a die with an uneven inner circumference; and in the case of forming the surface roughness of the entire coil body 23 in the same condition, the surface roughness of the proximal coil body 23b may be easily made higher than the surface roughness of the distal coil body 23a.

Fourth Embodiment

Next, a fourth embodiment of the present disclosure will be described. FIG. 6 is a distal end enlarged view of a guidewire of a fourth embodiment, and FIG. 7 is a distal end vertical sectional view of the guidewire of the fourth embodiment.

In the present embodiment, portions common to the first embodiment will be denoted by the same reference numerals, and descriptions of the portions will be omitted.

As shown in FIG. 6, a guidewire 30 of the present embodiment includes a core shaft 9, a coil body 33 covering a distal portion of the core shaft 9, and a coating agent 37 covering an outer periphery of the coil body 33.

The coil body 33 is a cylindrical hollow coil body formed by winding one or more metal wires, a distal end of the coil body 33 is joined to the core shaft 9 by brazing material 2, and a proximal end of the coil body 33 is joined to the core shaft 9 by brazing material 4.

The coil body 33 of the present embodiment is formed from two coil bodies consisting of a distal coil body 33a disposed on a distal side in the coil body 33 and a proximal coil body 33b disposed on a proximal side of the distal coil body 33a. Incidentally, a distal end of a wire included in the proximal coil body 33b of the present embodiment is joined to a proximal end of a wire included in the distal coil body 33a. Accordingly, a boundary between the distal coil body 33a and the proximal coil body 33b inclines obliquely along a twist angle of the coil body 33 as shown in FIGS. 6 and 7.

Further, a surface roughness of the proximal coil body 33b is higher than a surface roughness of the distal coil body 33a in the present embodiment. Incidentally, an area of the proximal coil body 33b is illustrated by hatching in FIGS. 6 and 7 in order to show that the surface roughness of the proximal coil body 33b is higher than the surface roughness of the distal coil body 33a.

Further, wires included in the distal coil body 33a and the proximal coil body 33b are rectangular in cross-section.

A material similar to that of the coil body 3 of the first embodiment may be used for the material of a wire included in the coil body 33. Stainless steel may be used in the distal coil body 33a and the proximal coil body 33b in the present embodiment.

The coating agent 37 covers the outer periphery of the coil body 33 and the core shaft 9 as described above, and the coating agent 37 of the present embodiment has a feature that the coating thickness of a range of the proximal coil body 33b is larger than the coating thickness of a range of the distal coil body 33a as shown in FIGS. 6 and 7.

Incidentally, the difference between the coating thickness of the range of the proximal coil body 33b and the coating thickness of the range of the distal coil body 33a in the present embodiment may be, for example, about several µm-10 µm, and it is illustrated exaggeratedly to facilitate understanding of the difference in FIGS. 6 and 7.

Since the surface roughness of the proximal coil body 33b is higher than the surface roughness of the distal coil body 33a, the coating thickness of the proximal coil body 33b becomes larger than the coating thickness of the distal coil body 33a.

Thereafter when the coating agent 37 is applied on the surface of the coil body 33, the coating thickness of the proximal coil body 33b automatically becomes larger than the coating thickness of the distal coil body 33a.

Also, it is capable of improving the adhesion between the proximal coil body 33b and the coating agent 37 and improving slidability of the guidewire 30.

On the other hand, it is capable of securing a good flexibility of the distal end of the guidewire 30 by applying the coating agent 37 in a thin layer on the distal coil body 33a at the distal side of the coil body 33.

Incidentally, the coating agent 37 may use the same material as the coating agent 7 of the first embodiment.

According to the guidewire 30 of the present embodiment, as a guidewire 30 comprises a core shaft 9, a coil body 33 covering a distal end portion of the core shaft 9, and a coating agent 37 covering an outer periphery of the coil body 33, wherein the coil body 33 includes a distal coil body 33a disposed on a distal side of the coil body 33, and a proximal coil body 33b disposed on a proximal side of the distal coil body 33a, and wires included in the distal coil body 33a and the proximal coil body 33b are rectangular cross-section, it is capable of forming thicker coating film of at least the proximal coil body 33b than before.

In particular, if the cross-sectional shape of the distal coil body 33a is circular, the effect is remarkable when an inner circumference of the distal coil body 33a is aligned with an inner circumference of the proximal coil body 33b.

The distal coil body 33a and the proximal coil body 33b in the present embodiments have been described as consisting of the same stainless steel. However, they may be set such that the hardness of the distal coil body 33a is lower than the hardness of the proximal coil body 33b, or grooves may be formed on the surface of wires included in the proximal coil body 33b along the longitudinal direction of the wires as described in the third embodiment, or they may be made by well-known surface treatment methods such as blasting processing being applied to the entire coil body 33 after masking a portion of the distal coil body 33a in the coil body 33 as described in the first embodiment.

In that case, in addition to the effect of the guidewire 30 of the present embodiment, the guidewire 30 may achieve effects of the guidewire of the first embodiment to the third embodiment.

Fifth Embodiment

Next, a fifth embodiment of the present disclosure will be described. FIG. 8 is a distal end vertical sectional view of a guidewire of a fifth embodiment.

In the present embodiment, portions common to the first embodiment will be denoted by the same reference numerals, and descriptions of the portions will be omitted.

As shown in FIG. 8, a guidewire 40 of the present embodiment includes a core shaft 9, a coil body 43 covering a distal portion of the core shaft 9, and a coating agent 47 covering an outer periphery of the coil body 43.

The coil body 43 is a cylindrical hollow coil body formed by winding one or more metal wires, a distal end of the coil body 43 is joined to the core shaft 9 by brazing material 2, and a proximal end of the coil body 43 is joined to the core shaft 9 by brazing material 4.

The coil body 43 of the present embodiment is formed from two coil bodies consisting of a distal coil body 43a disposed on a distal side in the coil body 43 and a proximal coil body 43b disposed on a proximal side of the distal coil body 43a. Incidentally, a distal end of a wire included in the proximal coil body 43b of the present embodiment is joined to a proximal end of a wire included in the distal coil body 43a. Accordingly, a boundary between the distal coil body 43a and the proximal coil body 43b inclines obliquely along a twist angle of the coil body 43 as shown in FIG. 8.

Further, a surface roughness of the proximal coil body 43b is higher than a surface roughness of the distal coil body 43a in the present embodiment. Incidentally, an area of the proximal coil body 43b is illustrated by hatching in FIG. 8 in order to show that the surface roughness of the proximal coil body 43b is higher than the surface roughness of the distal coil body 43a.

Further, wires included in the distal coil body 43a are circular in cross-section, and wires included in the proximal coil body 43b are rectangular in cross-section.

A material similar to that of the coil body 3 of the first embodiment may be used for the material of a wire included in the coil body 43. Stainless steel may be used in the distal coil body 43a and the proximal coil body 43b in the present embodiment.

The coating agent 47 covers the outer periphery of the coil body 43 and the core shaft 9 as described above, and the coating agent 47 of the present embodiment has a feature that the coating thickness of a range of the proximal coil body 43b is larger than the coating thickness of a range of the distal coil body 43a as shown in FIG. 8.

Incidentally, the difference between the coating thickness of the range of the proximal coil body 43b and the coating thickness of the range of the distal coil body 43a in the present embodiment may be, for example, about several μm-10 μm, and it is illustrated exaggeratedly to facilitate understanding of the difference in FIG. 8.

Since the surface roughness of the proximal coil body 43b is higher than the surface roughness of the distal coil body 43a, the coating thickness of the proximal coil body 43b becomes larger than the coating thickness of the distal coil body 43a.

Thereafter when the coating agent 47 is applied on the surface of the coil body 43, the coating thickness of the proximal coil body 43b automatically becomes larger than the coating thickness of the distal coil body 43a.

Also, it is capable of improving the adhesion between the proximal coil body 43b and the coating agent 47 and improving slidability of the guidewire 40.

On the other hand, it is capable of securing a good flexibility of the distal end of the guidewire 40 by applying the coating agent 47 in a thin layer on the distal coil body 43a at the distal side of the coil body 43.

Incidentally, the coating agent 47 may use the same material as the coating agent 7 of the first embodiment.

According to the guidewire 40 of the present embodiment, as a guidewire 40 comprises a core shaft 9, a coil body 43 covering a distal end portion of the core shaft 9, and a coating agent 47 covering an outer periphery of the coil body 43, wherein the coil body 43 includes a distal coil body 43a disposed on a distal side of the coil body 43, and a proximal coil body 43b disposed on a proximal side of the distal coil body 43a, and wires included in the distal coil body 33a are circular cross-section and wires included in the proximal coil body 33b are rectangular cross-section, it is capable of further improving flexibility of a distal end of the guidewire 40, since wires included in the distal coil body 43a tend to be in point contact each other.

The distal coil body 43a and the proximal coil body 43b in the present embodiments have been described as consisting of the same stainless steel. However, they may be set such that the hardness of the distal coil body 43a is lower than the hardness of the proximal coil body 43b, or grooves may be formed on the surface of wires included in the proximal coil body 43b along the longitudinal direction of the wires as described in the third embodiment, or they may be made by well-known surface treatment methods such as blasting processing being applied to the entire coil body 43 after masking a portion of the distal coil body 43a in the coil body 43 as described in the first embodiment.

In that case, in addition to the effect of the guidewire 40 of the present embodiment, the guidewire 40 may achieve effects of the guidewire of the first embodiment to the third embodiment.

DESCRIPTION OF THE CODE 1, 10, 20, 30, 40 . . . guidewire
2, 4 . . . brazing material
3, 13, 23, 33, 43 . . . coil body
3a, 13a, 23a, 33a, 43a . . . distal coil body
3b, 13b, 23b, 33b, 43b . . . proximal coil body
7, 17, 27, 37, 47 . . . coating agent
9 . . . core shaft
25 . . . groove

The invention claimed is:

1. A guidewire comprising:
a core shaft;
a coil body covering a distal end portion of the core shaft; and
a coating agent covering an outer periphery of the coil body, wherein
the coil body includes a distal coil body disposed on a distal side of the coil body, and a proximal coil body disposed on a proximal side of the distal coil body,
a groove is formed along a longitudinal direction of a wire included in the proximal coil body on a surface of the proximal coil body, wherein the groove is not formed on a surface of the distal coil body,
a surface roughness of the proximal coil body is higher than a surface roughness of the distal coil body, and
an outer diameter of the proximal coil body plus a thickness of the coating agent on the outer periphery of the proximal coil body is greater than an outer diameter of the distal coil body plus a thickness of the coating agent on the outer periphery of the distal coil body.

2. The guidewire according to claim 1 wherein
a plurality of the grooves is formed on the surface of the proximal coil body, and
the plurality of the grooves are not formed on the surface of the distal coil body.

3. The guidewire according to claim 1, wherein
the wire included in the proximal coil body has a rectangular shape in cross section.

4. The guidewire according to claim 3, wherein
a wire included in the distal coil body has a rectangular shape in cross section.

5. The guidewire according to claim 3, wherein
a wire included in the distal coil body has a circular shape in cross section.

6. The guidewire according to claim 1, wherein
the thickness of the coating agent on the outer periphery of the proximal coil body is greater than the thickness of the coating agent on the outer periphery of the distal coil body.

7. The guidewire according to claim 1, wherein
a hardness of the proximal coil body is greater than a hardness of the distal coil body.

8. A guidewire comprising:
a core shaft;
a coil body covering a distal end portion of the core shaft; and
a coating agent covering an outer periphery of the coil body, wherein
the coil body includes a distal coil body disposed on a distal side of the coil body, and a proximal coil body disposed on a proximal side of the distal coil body,
a surface roughness of the proximal coil body is higher than a surface roughness of the distal coil body,
an outer diameter of the distal coil body not including the coating agent is equal to an outer diameter of the proximal coil body not including the coating agent, and
the outer diameter of the proximal coil body plus a thickness of the coating agent on the outer periphery of the proximal coil body is greater than the outer diameter of the distal coil body plus a thickness of the coating agent on the outer periphery of the distal coil body.

9. A guidewire comprising:
a core shaft;
a coil body covering a distal end portion of the core shaft; and
a coating agent covering an outer periphery of the coil body, wherein
the coil body includes a distal coil body disposed on a distal side of the coil body, and a proximal coil body disposed on a proximal side of the distal coil body,
a surface roughness of the proximal coil body is higher than a surface roughness of the distal coil body, and
an outer diameter of the proximal coil body plus a thickness of the coating agent on the outer periphery of the proximal coil body is greater than an outer diameter of the distal coil body plus a thickness of the coating agent on the outer periphery of the distal coil body.

* * * * *